(12) United States Patent
Chiang

(10) Patent No.: US 11,357,656 B2
(45) Date of Patent: Jun. 14, 2022

(54) HALO VESTS AND CONSTRUCTION METHODS THEREOF

(71) Applicant: ORION BIOTECH INC., Taipei (TW)

(72) Inventor: Ming-Fu Chiang, Taipei (TW)

(73) Assignee: ORION BIOTECH INC., Taipei (TW)

( * ) Notice: Subject to any disclaimer, the term of this patent is extended or adjusted under 35 U.S.C. 154(b) by 428 days.

(21) Appl. No.: 16/462,529

(22) PCT Filed: Dec. 29, 2016

(86) PCT No.: PCT/CN2016/113035
§ 371 (c)(1),
(2) Date: May 20, 2019

(87) PCT Pub. No.: WO2018/094820
PCT Pub. Date: May 31, 2018

(65) Prior Publication Data
US 2019/0274865 A1   Sep. 12, 2019

(30) Foreign Application Priority Data

Nov. 25, 2016   (CN) .......................... 201611055281.6

(51) Int. Cl.
*A61F 5/055* (2006.01)
*A61F 5/058* (2006.01)
*A61F 5/048* (2006.01)
*B33Y 80/00* (2015.01)

(52) U.S. Cl.
CPC .......... *A61F 5/05891* (2013.01); *A61F 5/048* (2013.01); *A61F 5/055* (2013.01); *B33Y 80/00* (2014.12)

(58) Field of Classification Search
CPC .. A61F 5/02; A61F 5/026; A61F 5/042; A61F 5/048; A61F 5/05; A61F 5/055; A61F 5/05883; A61F 5/3707; A61F 5/05891; A61H 1/0218; A61H 1/0292; A61H 1/0296; B33Y 80/00
See application file for complete search history.

(56) References Cited

U.S. PATENT DOCUMENTS

| 3,957,040 A | * | 5/1976 | Calabrese | ............... A61F 5/055 602/17 |
| 4,541,421 A | | 9/1985 | Iversen et al. | |
| 5,010,881 A | | 4/1991 | Boudreau et al. | |
| 5,302,170 A | * | 4/1994 | Tweardy | ................. A61F 5/055 602/17 |

(Continued)

FOREIGN PATENT DOCUMENTS

| CN | 201701350 U | 1/2011 |
| CN | 102245134 A | 11/2011 |

(Continued)

*Primary Examiner* — Camtu T Nguyen
(74) *Attorney, Agent, or Firm* — Cheng-Ju Chiang

(57) ABSTRACT

Halo vests and the construction methods thereof are provided. The halo vests are designed in unibody structures to minimize the number of components. A 3D scanner is utilized to scan a subject to obtain parameters for a modeling program, which help to construct an optimized halo vest for the subject by printing rather than assembling manually. The subject can easily put on the halo vest without miscellaneous steps.

10 Claims, 6 Drawing Sheets

(56) References Cited

U.S. PATENT DOCUMENTS

| | | | | |
|---|---|---|---|---|
| 5,697,895 A | * | 12/1997 | Bremer | A61F 5/055 602/37 |
| 5,715,541 A | * | 2/1998 | Landau | A41D 13/05 2/410 |
| 5,832,926 A | | 11/1998 | Towlen | |
| 2002/0068889 A1 | * | 6/2002 | Bonutti | A61F 5/02 602/18 |
| 2002/0151831 A1 | | 10/2002 | Stamper et al. | |
| 2010/0138193 A1 | | 6/2010 | Summit et al. | |
| 2011/0118639 A1 | * | 5/2011 | Tweardy | A61F 5/055 602/18 |
| 2013/0226055 A1 | | 8/2013 | Akpotaire et al. | |
| 2015/0328038 A1 | * | 11/2015 | Rosenfeld | A61F 5/055 602/18 |

FOREIGN PATENT DOCUMENTS

| | | |
|---|---|---|
| CN | 102319133 A | 1/2012 |
| CN | 202665916 U | 1/2013 |
| CN | 203468825 U | 3/2014 |
| CN | 103800109 A | 5/2014 |
| CN | 104665970 A | 6/2015 |
| CN | 205322580 U | 6/2016 |
| CN | 106073964 A | 11/2016 |
| TW | M316066 U | 8/2007 |

\* cited by examiner

HALO VESTS AND CONSTRUCTION METHODS THEREOF

CROSS-REFERENCE TO RELATED APPLICATION AND CLAIM OF PRIORITY

This application is a 35 U.S.C. § 371 National Phase conversion of International (PCT) Patent Application No. PCT/CN2016/113035, filed on Dec. 29, 2016, which claims the benefit of Chinese Patent Application No. 201611055281.6, filed on Nov. 25, 2016, the disclosure of which is incorporated herein in its entirety by reference.

1. Technical Field

At least one embodiment of the present invention provides equipment in the art of rehabilitation for spines. More particularly, the equipment used externally during surgeries or after injuries to provide spinal traction or spinal rehabilitation.

2. Description of The Related Art

Spinal injuries are commonly induced by motor vehicle accidents and falls as well. More particularly, induced by the subsequent fractures, dislocates, or crushes of vertebrae or damages to the spinal nerve. Upon spinal injuries, cervical spine may lose the ability to provide supporting force and thus places the patients in extremely fragile conditions. In the 1930s, traction tables were developed to stabilize patients and avoid subsequent damages to spine. However, long-term use of the traction tables usually comes with bedsores and muscular dystrophy. Later in 1959, Vernon Nickel and Jacqueline Perry proposed a wearing device comprises a halo connecting to an on-shoulder scaffold surrounding the head of a patient. The wearing device frees patients from bed rest which largely induces bedsores and muscular dystrophy. However, the strength and stability of the wearing device are not satisfying. On the other hand, cast vests, an alternative method, limit the rotation of neck and may indirectly induce damages to the cervical spine.

The most common device used today is the halo vests. A halo vest primarily comprises a halo with skull pins, a plastic vest, and adjustable metal bars connecting between the halo and the vest. Minor elements in the halo vest include nuts, bolts, belts, straps, and the inner lining of the vest. With a halo vest, the patient could perform daily activities, including standing and walking, with less limitations in motion. The halo vests reduce the need of bed rest and provide stronger mobility as compared to cast vests and traction forceps.

The disadvantages of halo vests include that numerous elements (e.g., the fasteners between the halo, the adjustable metal bars, and the vest) are used in the assembly. A patient requires additional time and external assistance to assemble a halo vest on the body. Problems such as fastener loosening and component dislocating are commonly found in halo vests. Moreover, the halo requires four skull pins anchoring at the skull. The wounds on forehead largely affect the appearance of patients. And any force applied on the skull pins would cause pain and uncomfortable feelings to the patients. Except the skull pins, other components of halo vests usually are recycled and reused on the next patient. In addition to the hygiene issues, halo vests may not be applicable to patients with different figures and body shapes.

SUMMARY

At least one embodiment of the present invention provides a halo vast to mitigate the aforementioned problems.

The halo vest comprises a halo, a supporter, a vest, and a strap. The halo is configured to span a head from one lateral side of the head to another. Each side of the halo comprises a holder, wherein the interior side of the holder is arc-shaped. The supporter is horseshoe-shaped. On the interior side at the top of the supporter, a bridge is configured thereon and is connected with the holder. The vest comprising a frontal region and a posterior region. The upper part of the vest is connected with the supporter, and the lower part of the vest comprises engaging holes configured on each end of both the frontal region and the posterior region. The strap comprising engaging elements at each end, in which the engaging elements are configured to be paired with the engaging holes.

The halo is configured to provide traction force. In order to match the shape of a head, the halo is preferred to be arc-shaped or horseshoe-shaped. In some embodiments, the supporter comprises at least one rib at each side to improve the strength of the supporter. The frontal region and the posterior region of the vest are both in U-shape, K-shape, or H-shape. In order to be attached on the vest, the engaging elements are in U-shape or H-shape.

The holder is arc-shaped to match the shape of a head, while the interior surface of the bridge is arc-shaped or flat. In some preferred embodiments that the holder is arc-shaped, the exterior surface of the holder is made as an arc to match the interior surface of a bridge which is also arc-shaped. In some other embodiments that the holder is arch-shaped, the interior surface of the holder is made as an arc to match a head while the exterior surface of the holder is flat to match the interior surface of a bridge which is also flat. Moreover, the left wing and the right wing of the holder each may comprise at least one first fastener. Similarly, the left wing and the right wing of the bridge each may comprise at least one second fastener. The at least one first fastener and the at least one second fastener in alignment may be fastened with bolts to connect the holder and the bridge. The two ends of the holder may each comprise a least one thread hole. With the thread holes, skull pins may be used to secure the halo on the head. The configuration of thread holes is preferred to avoid obvious wounds on forehead.

In some embodiments, the halo is unibody while the supporter and the vest together are also unibody. Moreover, the halo, the supporter, and the vest may be made of plastic materials. The halo vast made of plastic materials contain the chest and back of a user to fix the upper part of body and the head in the same position.

Accordingly, some embodiments of the present invention widely use unibody structures to reduce the number of components of halo vests. The halo vests comprise a halo in a unibody structure and a vest in combination with a supporter in horseshoe-shaped in another unibody structure. As that the supporter and the vest are unibody, no connectors or fasteners are required for the interconnection thereof. Moreover, the unibody design avoid loosening of fasteners and the dislocating of the supporter and the vest. Accordingly, the halo vests are constructed in firm and stable structures. Another advantage of the unibody design is that a user can apply and secure the halo vest with reduced steps and configuration. Yet another advantage of the unibody design is that the halo vests are suitable for 3D printing. A customized halo vest can be manufactured in a relative short of time.

At least one embodiment of the present invention provides construction methods of halo vests. The construction methods comprise a step of establishing a modeling program, a step of scanning a body by a 3D scanner to obtain parameters, a step of performing the modeling program, a step of selecting the design of a halo vest provided in one of any embodiments, a step of providing the parameters to obtain a 3D image file, and a step of activating a 3D printer for construction based on the 3D image file.

In some embodiments, the parameters in the step of scanning are selected from the group consisting of a head size, a shoulder width, a chest width, a neck width, the distance and between the widest bilateral line of head and the shoulder, and curvatures. After the step of scanning, the obtained parameters are provided to the modeling program to create a 3D image corresponding real object. The 3D printer then constructs a halo vest based on the 3D image. To wear the halo vest, the halo vest is applied onto a user and then fasten the bolts and secure the skull pins. Under the condition that a user prefers to choose another design from another embodiment, the process may return to the step of selecting in the construction methods. Under the condition that the obtained parameters are invalided, the process may return to the step of scanning in the construction methods. As such, the 3D printing technique used in the embodiments may construct a customized halo vest for each user or an easy-to-wear and disposable halo vest in 2 hours.

DESCRIPTION OF THE PREFERRED EMBODIMENTS

The examples depicted in the following section are provided for the purpose of detailed explanation of the features of preferred embodiments, in order to enable one having ordinary skill in the art to understand the preferred embodiments.

Figure 1:
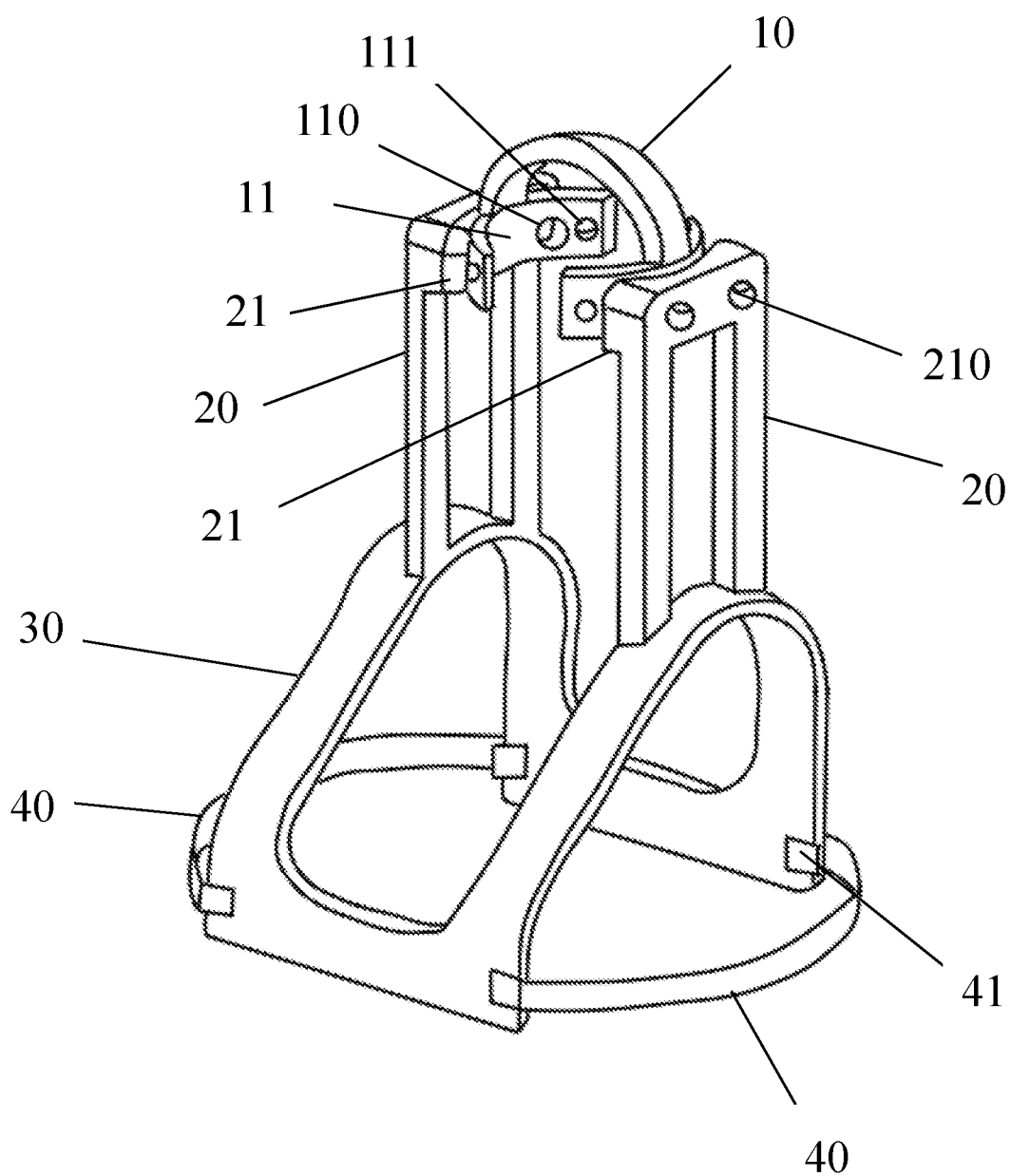
FIG. 1 is a diagram illustrating a halo vest, in accordance with the first embodiment of the present invention.
Figure 2:
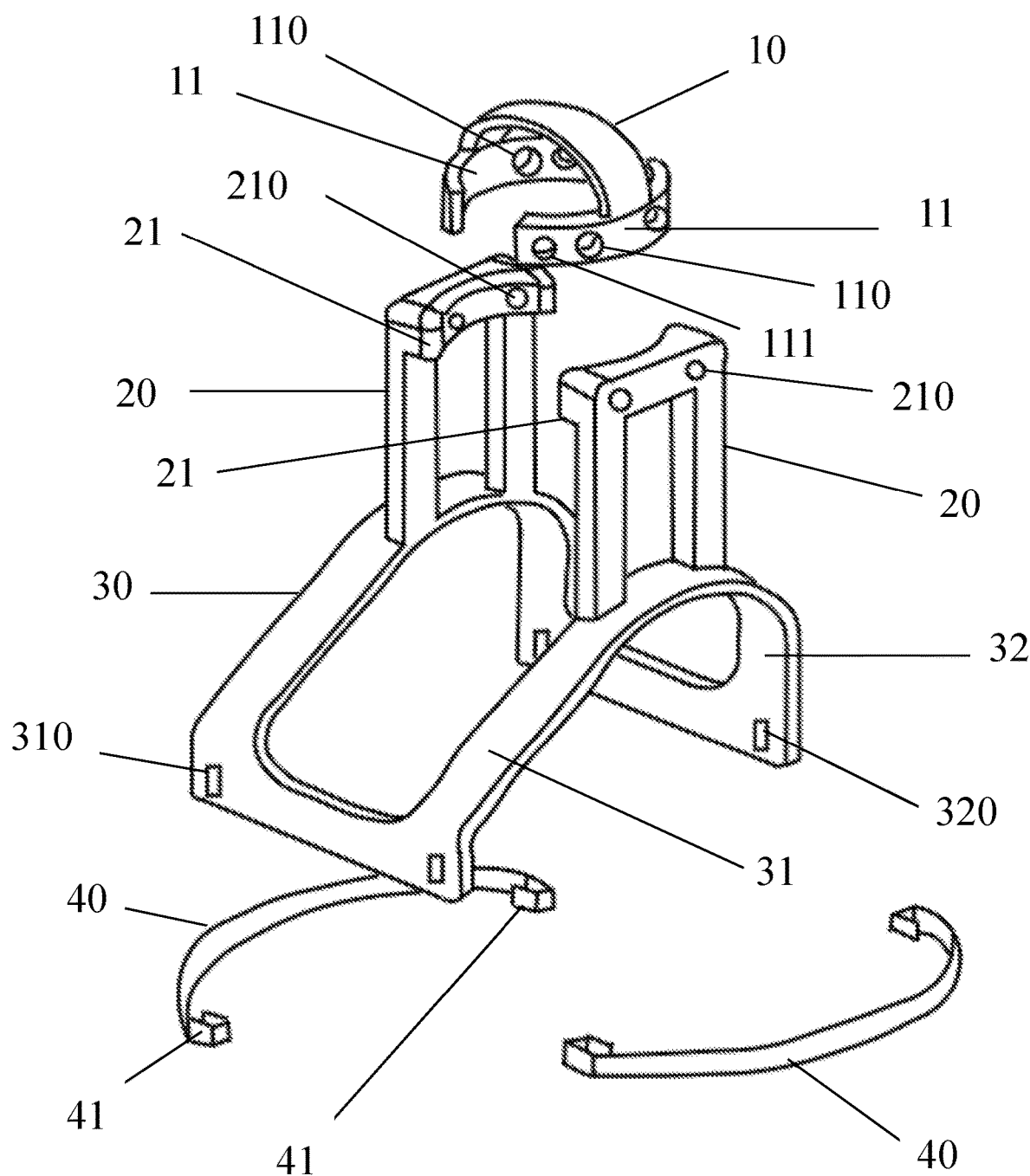
FIG. 2 is another diagram illustrating the halo vest, in accordance with the first embodiment of the present invention.

Referring to FIG. 1 and FIG. 2. FIG. 1 is a diagram illustrating a halo vest, in accordance with the first embodiment of the present invention. FIG. 2 is another diagram illustrating the halo vest, in accordance with the first embodiment of the present invention. The halo vest 1 comprises a halo 10 configured to span a head from one lateral side of the head to another, a supporter 20 in horseshoe-shaped, a vest 30 comprising a frontal region 31 and a posterior region 32, and a strap 40. Each end of the halo 10 comprises a holder 11 having an interior surface as an arc. The interior side at the top of the supporter 20 is configured with a bridge 21, in which the interior surface of the bridge 21 is arc-shaped. The upper part of the vest 30 is connected with the supporter 20, and the lower part of the vest 30 comprises engaging holes 310, 320 at each end of both the frontal region 31 and the posterior region 32. The two ends of the strap 40 are each configured with an engaging element 41 pairing with the engaging holes 310, 320. The holder 11 is connected with the bridge 21 and the bilateral sides of the vest 30 are each linked by a strap 40.

The halo 10 is configured to provide traction force. The halo 10 is arc-shaped in order to fit in the shape of a head. In some other embodiments, the halo 10 is in horseshoe-shaped. The halo 10 and the holder 11 are integrated as a unibody structure. The two ends of the holder 11 are each configured with a thread hole 111. With the thread holes 111, skull pins may be used to secure the halo 10 on the head. The configuration of thread holes 111 avoids obvious wounds on the forehead. The left wing and the right wing of the holder 11 each comprises a first fastener 110, while the left wing and the right wing of the bridge 21, configured at the top of the support 20, each comprises a second fastener 210. The first fasteners 110 and the second fasteners 210 are in alignment, thus bolts can fasten the holder 11 and the bridge 21 through the first fasteners 110 and the second fasteners 210.

In some embodiments, the holder 11 is arc-shaped while the interior surface of the bridge 21 is also arc-shaped. The holder 11 and the bridge 21 therefore could match and fit with each other. In some other embodiments that the holder 11 is arch-shaped, the interior surface of the holder 11 would also be made as an arc to match a head. However, both the exterior surface of the holder 11 and the interior of the surface of the supporter 21 are flat in order to match and fit with each other.

The vest 30 is made in a unibody structure. The frontal region 31 and the posterior region 32 are both U-shaped and corresponding to each other. The engaging elements 41 are preferred to be U-shaped, for the strap 40 to be conveniently attached to the vest 30. However, the engaging elements 41 are not limited to be U-shaped. An engaging element 41 may be H-shaped or in some other shapes as long as the strap 40 could firmly attach to the vest 30. The halo 10, the supporter 20, and the vest 30 may be made of plastic materials. The harden plastic materials help to cage the chest and back of a user to fix the upper part of body and the head in the same position.

The supporter 20 is preferred to be horseshoe-shaped, where the space between two arms is wider than the ear. The supporter 20 is configured on the vest 30. A pair of supporters 20 is preferred to be configured closely to the bilateral sides of the head, and the height of the supporter 20 is determined based on the distance between the shoulder and skull pins. The height of the vest 30 is determined based on the distance between the chest and the shoulder, and the width is determined based on the chest width or the distance between two armpits. The strap 40 is preferred to be configured at a place above the waist and close to the chest.

Some embodiments of the present invention widely applied unibody structures to reduce the number of components of halo vests. The halo 10 is the first unibody structure. The supporter 20 in horseshoe-structure is the second unibody structure. The supporter 20 and the vest 30 together are the third unibody structure. Accordingly, the unibody design reduce risks including loosening of fasteners and dislocating of the components. The halo vests are therefore strong and stable. Another advantage of the unibody design is that the user can apply and secure the halo vest with reduced steps and helps. With the unibody structures, the 3D printing technique can be applied to construct an easy-to-wear and disposable halo vest 1 in a short time.

Figure 3:
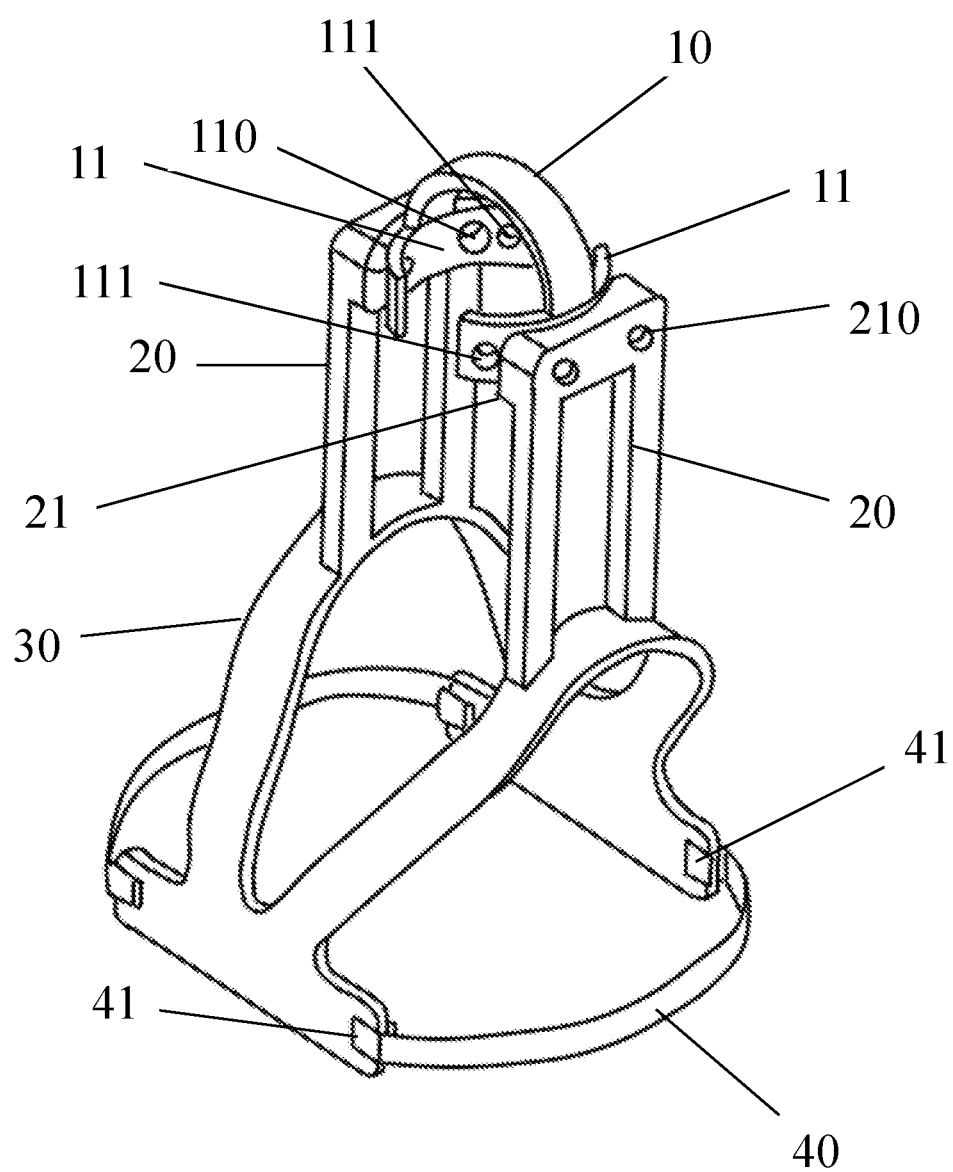
FIG. 3 is a diagram illustrating a halo vest, in accordance with the second embodiment of the present invention.
Figure 4:
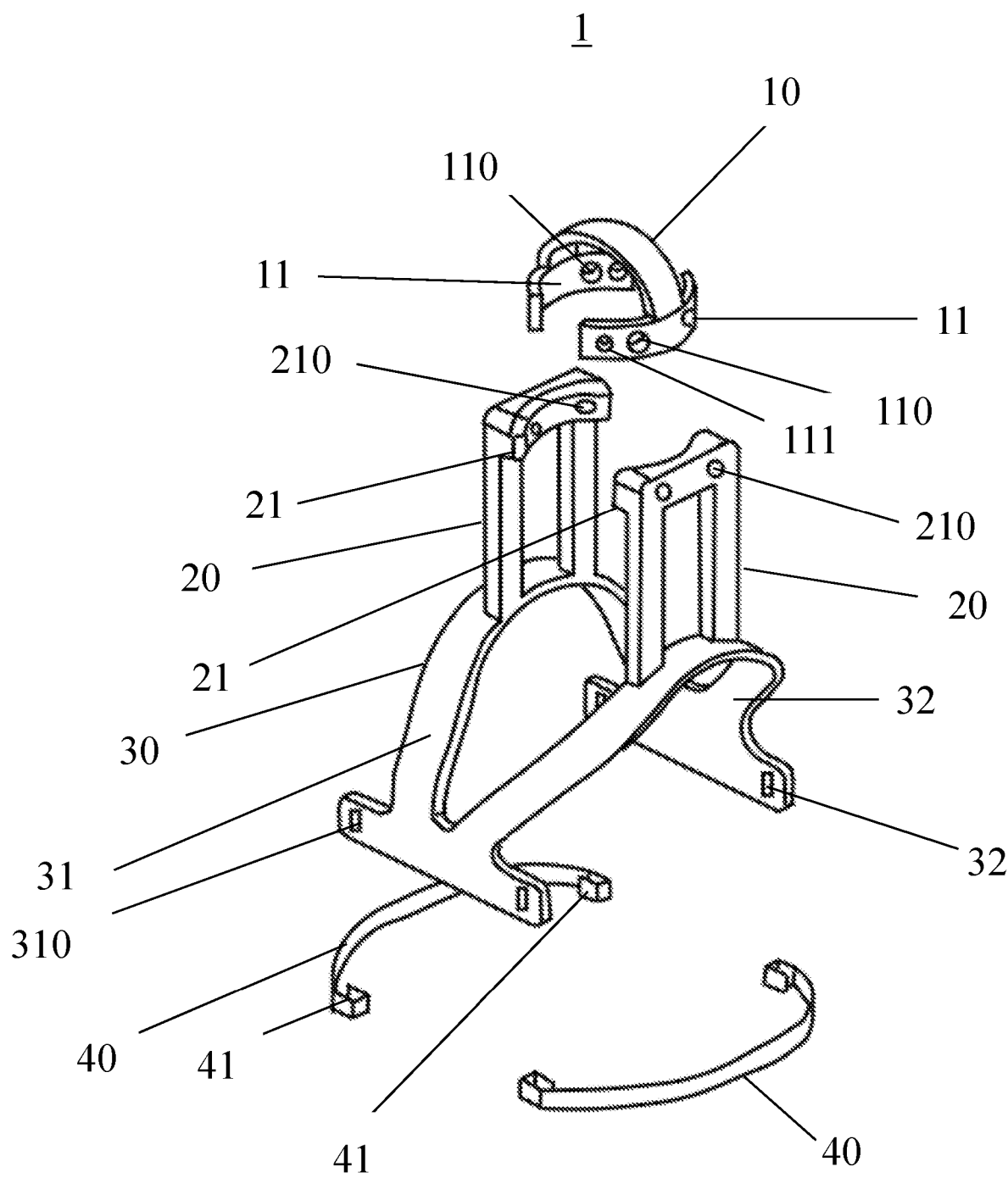
FIG. 4 is another diagram illustrating the halo vest, in accordance with the second embodiment of the present invention.

Referring to FIG. 3 and FIG. 4. FIG. 3 is a diagram illustrating a halo vest, in accordance with the second embodiment of the present invention. FIG. 4 is another diagram illustrating the halo vest, in accordance with the second embodiment of the present invention. The overall configuration is similar to the embodiment in FIG. 1. However, the frontal region 31 and the posterior region 32 are substituted with K-shaped structures. In addition to the U-shaped structure used in FIG. 1 and the K-shaped structure used in FIG. 3, the frontal region 31 and the posterior region 32 may be in H-shape structures.

Figure 5:
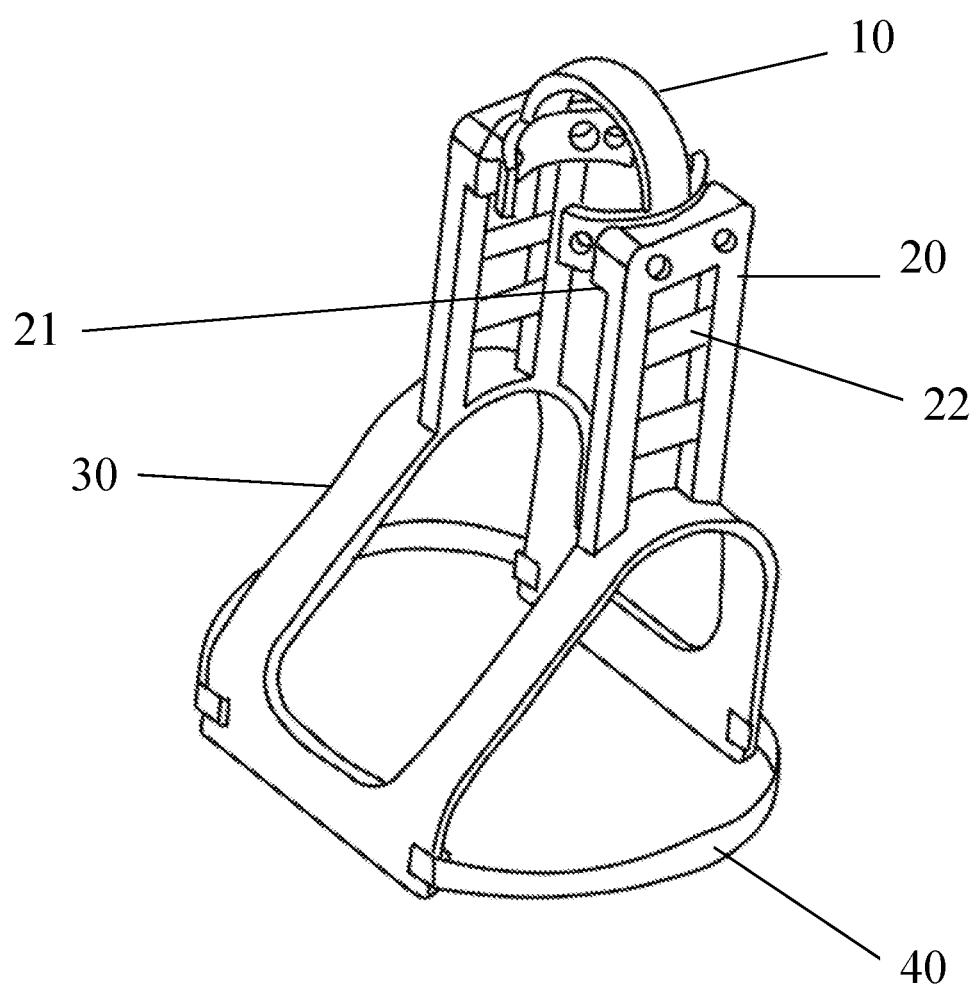
FIG. 5 is a diagram illustrating a halo vest comprising ribs, in accordance with some embodiments of the present invention.

FIG. 5 is a diagram illustrating a halo vest comprising ribs, in accordance with some embodiments of the present invention. As illustrated in FIG. 5, at least one rib 22 can be installed in the supporter 20 to improve the strength of supporter 20.

Figure 6:
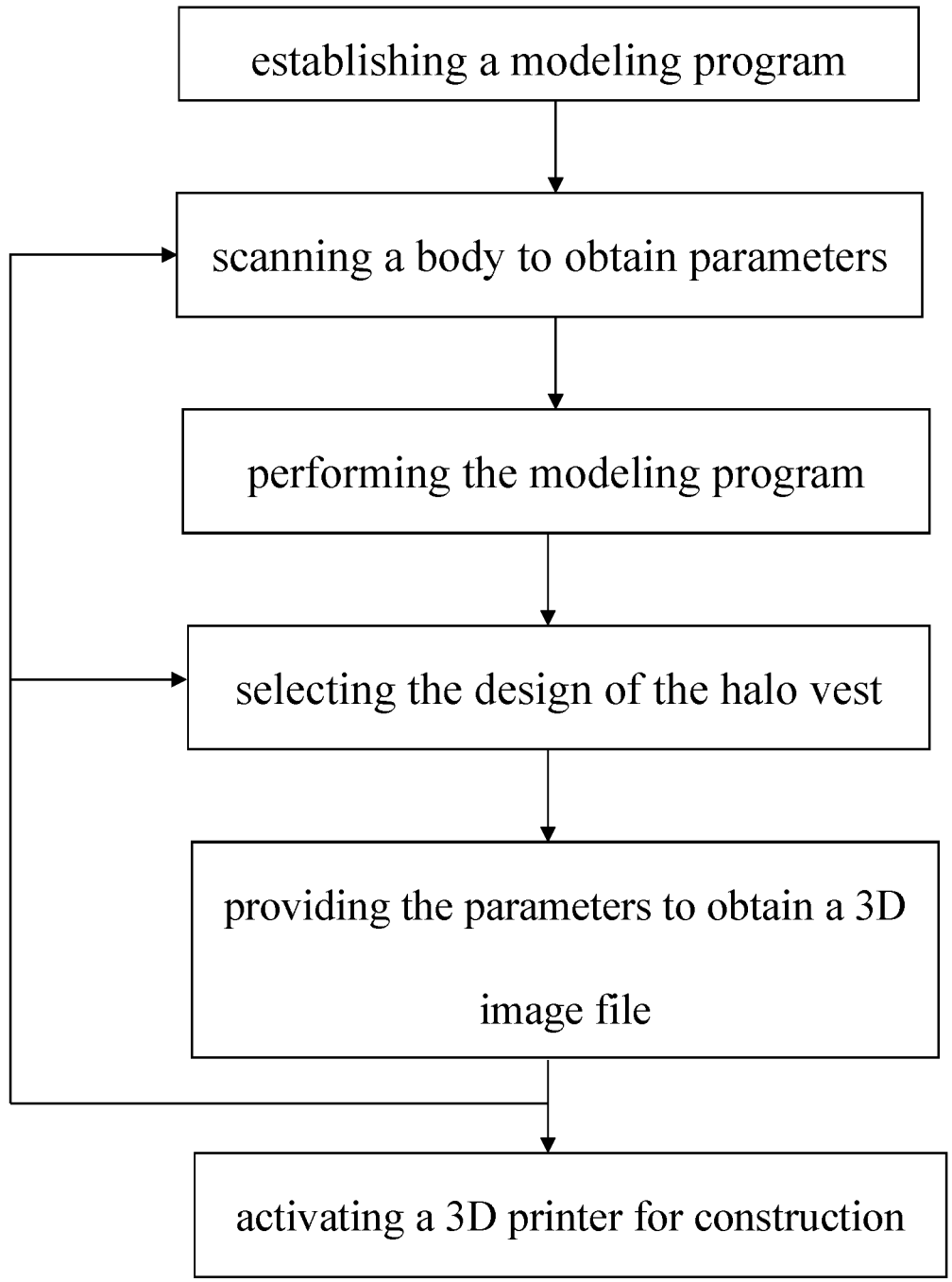
FIG. 6 is a flowchart illustrating a construction method of halo vests, in accordance with some embodiments of the present invention.

FIG. 6 is a flowchart illustrating a construction method of halo vests, in accordance with some embodiments of the present invention. At least one embodiment of the present invention provides construction methods of halo vest. The construction methods comprise a step of establishing a modeling program, a step of scanning a body by a 3D scanner to obtain parameters, a step of performing the modeling program, a step of selecting the design of a halo vest provided in any embodiments, a step of providing the parameters to obtain a 3D image file, and a step of activating a 3D printer for construction based on the 3D image file.

As illustrated in FIG. 6, after the step of establishing the modeling program, a 3D scanner is used to obtain parameters including the head size, shoulder width, chest width, neck width, distance between the widest bilateral line of the head and the shoulder, and curvatures. The parameters are then provided to the model program in the step of providing to obtain a 3D image file mirroring the real object. In the step of activating, a 3D printer constructs a product in accordance with the 3D image file. The product can be applied on a subject and then secure with bolts and skull pins. Under the condition that a user prefers to choose another design from another embodiment, the process may return to the step of selecting in the construction methods. Under the condition that the obtained parameters are invalided, the process may return to the step of scanning in the construction methods.

Accordingly, the 3D printing technique used in the embodiments may construct a customized halo vest for each user or a disposable but comfortable halo vest in 2 hours.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A halo vest, comprising:
    a halo configured to span a head from one lateral side of the head to another, wherein each side of the halo comprises a holder, wherein the holder is comprised of two holder units, and wherein each inner side of the two holder units is arc-shaped;
    a supporter which is horseshoe-shaped, wherein a pair of bridge units is configured onto the supporter and sticks out from each inner side of the supporter, and wherein the pair of bridge units is connected with the holder;
    a vest comprising a frontal region and a posterior region, wherein the vest is connected with the supporter, and wherein engaging holes at each end of both the frontal region and the posterior region are disposed below the vest; and
    a strap comprising engaging elements at each end, wherein the engaging elements are configured to be paired with the engaging holes;
    wherein the halo is unibody;
    wherein the supporter and the vest are unibody;
    wherein the halo vest is constructed by a 3D printer based on a 3D image file.

2. The halo vest as claimed in claim 1, wherein the halo is arc-shaped or horseshoe-shaped.

3. The halo vest as claimed in claim 1, wherein each end of the two holder units comprises at least one thread hole.

4. The halo vest as claimed in claim 1, wherein the two holder units are arc-shaped.

5. The halo vest as claimed in claim 1, wherein each inner side of the bridge is arc-shaped or flat.

6. The halo vest as claimed in claim 1, wherein the supporter comprises at least one rib.

7. The halo vest as claimed in claim 1, wherein the two holder units each comprises at least one first fastener, and wherein the pair of the bridge units each comprises at least one second fastener, and wherein the at least one first fastener is aligned with the at least one second fastener.

8. The halo vest as claimed in claim 1, wherein the frontal region and the posterior region are both in U-shape, K-shape, or H-shape.

9. The halo vest as claimed in claim 1, wherein the engaging elements are in U-shape or H-shape.

10. The halo vest as claimed in claim 1, wherein the halo, the supporter, and the vest are made of plastic materials.

* * * * *